(12) United States Patent
Vaccaro (10) Patent No.: US 7,197,830 B2
(45) Date of Patent: Apr. 3, 2007

(54) ALIGNMENT QUALITY INDICATOR (75) Inventor: Christopher M. Vaccaro, Ofallon, MO (US)

(73) Assignee: The Boeing Company, Chicago, IL (US)

( * ) Notice: Subject to any disclaimer, the term of this patent is extended or adjusted under 35 U.S.C. 154(b) by 84 days.

(21) Appl. No.: 11/084,653

(22) Filed: Mar. 18, 2005

(65) Prior Publication Data
US 2006/0207116 A1 Sep. 21, 2006

(51) Int. Cl.
G01B 21/22 (2006.01)
(52) U.S. Cl. .......................... 33/286; 33/533; 378/205; 378/207
(58) Field of Classification Search ................. 33/286, 33/533, 520, 644–645; 378/205–207, 58, 378/162–164
See application file for complete search history.

(56) References Cited

U.S. PATENT DOCUMENTS

| 2,496,099 | A | * | 1/1950 | Leto ............................. 33/1 R |
| 3,374,350 | A | * | 3/1968 | Mills, Jr. .................... 378/205 |
| 3,699,474 | A | * | 10/1972 | Landry ........................ 372/17 |
| 4,048,507 | A | * | 9/1977 | de Gaston .................. 378/162 |
| 4,578,806 | A | * | 3/1986 | Grass et al. ................. 378/162 |
| 5,210,783 | A | * | 5/1993 | Wallace ....................... 378/207 |
| 5,402,577 | A | | 4/1995 | Cumings |
| 5,561,696 | A | * | 10/1996 | Adams et al. ................ 378/58 |
| 5,644,616 | A | * | 7/1997 | Landi et al. ................. 378/206 |
| 5,878,072 | A | * | 3/1999 | Greisz ......................... 372/103 |
| 6,459,772 | B1 | * | 10/2002 | Wiedenhoefer et al. .... 378/163 |
| 2003/0091145 | A1 | * | 5/2003 | Mohr et al. .................. 378/58 |

* cited by examiner

Primary Examiner—Diego Gutierrez
Assistant Examiner—Tania Courson
(74) Attorney, Agent, or Firm—Ingrassia Fisher & Lorenz, P.C.

(57) ABSTRACT

An alignment tool includes a base, a column, and a ball. The base is manufactured from a material with a high material density and includes a crosshair. The column is machined out of an optical transparent material and is attached to the base. The ball is positioned within the column at the end opposite to the base and above the center of the crosshair. The alignment tool may not only be used to properly align a radiation source with an area of interest of a part to be inspected but also as an alignment quality indicator providing information of proper alignment to an interpreter of the radiograph taken. Therefore, the need to take multiple exposures can be eliminated. The alignment quality indicator is suitable for, but not limited to, applications in the aerospace industry, such as nondestructive testing and evaluation of airframes during aircraft manufacturing, maintenance, and repair.

23 Claims, 8 Drawing Sheets

ALIGNMENT QUALITY INDICATOR

BACKGROUND OF THE INVENTION

The present invention generally relates to radiographic inspection techniques and, more particularly, to an alignment tool and to a radiographic inspection process.

Radiographic inspection techniques have been used for over half a century for nondestructive testing of weld, castings, and forgings in a variety of industries. Radiographic inspection techniques are currently used, for example, for the evaluation of aging and contemporary aircraft, as well as during aircraft manufacturing, maintenance, and repair. Radiographic inspection may be employed beneficially to detect hidden defects, such as cracks, gaps, and corrosion, to assess internal damage, and to detect foreign objects, for example, in airframe structures. Aircraft nondestructive inspection and evaluation eliminates the need for unnecessary maintenance and aircraft disassembly, which has the potential for creating additional damage and repair problems. High-energy radiation can be used to study the condition of aircraft structure. Gamma rays from absorbed materials and x-rays from vacuum tubes are the type of energy source used for radiographic inspection techniques. The function of an x-ray tube is to convert electrical energy into x-rays. The output of the tube is rated in kilovolts. Most aircraft tubes run approximately 150 kilovolts, a relatively modest energy level. Energy waves pass through the metal undergoing irradiation and some of the energy is absorbed in that process. The amount of absorption is dependent upon the density and thickness of the metal. The differences in the absorption are usually measured by exposure to radiographic film. The exposed radiographic film, also called radiograph, is the heart of a radiographic inspection. A radiographic film is composed of a sheet of clear cellulose or triacetate that is treated on both sides with an emulsion of gelatin and silver halide compounds. When exposed to x-radiation, gamma rays, or light, these silver halide compounds undergo a chemical change. When the exposed film is treated in a chemical solution (developer), further reaction takes place. The silver halide compounds form tiny crystals of black metallic silver. It is this silver, suspended in gelatin on both sides of the triacetate base, that forms the radiographic image. The film then resembles a photographic negative. Thinner sections of material will appear darker than thicker ones. On a radiograph, the areas most severely pitted, exfoliated, or affected by intergranular attack will appear darker than the rest of a test specimen.

The correct interpretation of the radiograph depends essentially on the image quality and the interpreter's experience in his evaluation. The image quality depends significantly on the achievement of proper alignment of the x-ray or gamma ray source with the intended condition, such as a material defect. Traditional methods to align the x-ray or gamma ray source, for example, the x-ray tube with the condition require a stepped process. During this alignment process the radiographic film is placed on the part to be irradiated, the x-ray tube is energized, the radiographic film is processed, the radiograph is evaluated, and adjustments are then made to the location of the x-tube before the next exposure. This process needs to be repeated as many times as necessary to achieve the desired image quality. Each exposure cycle takes on average 20 to 40 minutes, which is included in cycle times and reflects in manufacturing or inspection cost of the product, for example an aircraft airframe. As engineering requirements currently approach tighter defect widths, the x-ray or gamma ray source to condition alignment becomes more critical thus increasing the number of exposures needed to obtain desired image quality of the radiograph.

Furthermore, the alignment quality feedback to the interpreter of the radiograph, such as an inspector or technician, is crucial for the evaluation of the radiograph. Currently, inspectors typically measure a geometric feature of known size on the exposed and developed radiographic film to determine alignment quality. This approach creates problems due to geometric magnification, x-ray or gamma ray source to part distance, and focal spot size.

Presently available radiographic tools, such as x-ray tubes, are designed to project a laser image corresponding with the central ray emitted by the radiographic tool when energized. This laser-sighting feature is very useful to the technician in approximating alignment between the central x-ray or gamma ray and the median point of the part to be imaged. Currently the laser may not be used for precise alignment of the radiographic tool.

Prior art includes various radiographic inspection aids, for example, U.S. Pat. No. 5,402,577, issued to Cummings. The described radiographic inspection aid can be used for the radiographic inspection of electron beam welds. The described radiographic inspection aid enables one-dimensional alignment of an x-ray tube, but cannot be used as an alignment quality indicator. The disclosed prior art inspection aid is used as an angle alignment tool which assists in ensuring that x-rays aimed at welds during inspection penetrate the weld seam at an angle of approximately 90 degrees measurable against the surface of the weld along both its length and width. Even though it may be possible to use the prior art alignment aid to align an x-ray tube, it is not possible to use the prior art inspection aid to verify the alignment quality due to the poor radiographic qualities of the alignment aid.

As can be seen, there is a need for an alignment aid that eliminates the currently used stepped alignment process of the radiation source, for example, an x-ray tube, and, consequently, reduces the inspection cycle time. Furthermore, there is a need for an alignment aid that improves the alignment quality feedback to the interpreter of the radiographs and provides a permanent record of the exposure.

There has, therefore, arisen a need to provide an alignment tool that enables the accurate alignment of a radiation source used during radiographic inspection to a condition to be inspected without the need to take multiple exposures. There has further arisen a need to provide an alignment tool that enables three-dimensional alignment of a radiation source, such as an x-ray tube, to a condition that allows the detection and identification of small width defects in the irradiated part. There has still further arisen a need to provide feedback to the inspector that the alignment was correct for the exposure thus improving inspection confidence.

SUMMARY OF THE INVENTION

The present invention provides an alignment tool that may be used during radiographic inspection to achieve proper alignment of a radiation source with the part to be inspected. The present invention further provides an alignment quality indicator that provides accurate feedback to an interpreter of the radiographs thus improving inspection confidence. The present invention provides an alignment quality indicator that is suitable for, but not limited to, applications in the aerospace industry, such as nondestructive testing and evaluation of airframes during aircraft manufacturing, maintenance, and repair. The alignment quality indicator may be used, for example, for crack and or gap detection during fastener inspection on aircraft airframes using radiographic techniques.

In one aspect of the present invention, an alignment tool comprises a base, a column, and a ball. The base includes a crosshair having a center. The column is machined from an optically transparent material and has a first end and a second end. The first end of the column is attached to the base and the crosshair is visible from the second end of the column. The ball is positioned within the column at the second end and above the center of the crosshair.

In another aspect of the present invention, an alignment quality indicator comprises a radiation source having a focal point, a laser, an alignment tool, and a radiographic detector. The laser is aligned with the focal point of the radiation source. The laser emits a laser beam. The alignment tool includes a base manufactured from a material having a high material density, a column machined from an optically transparent polymer material and having a first end and a second end, and a ball positioned within the column at the second end and above the center of the crosshair. The base includes a crosshair having a center. The first end of the column is attached to the base. The crosshair is visible from the second end of the column. The laser beam is pointed at the ball. The alignment tool is positioned between the radiation source and the radiographic detector.

In a further aspect of the present invention, a radiographic inspection process comprises the steps of: placing an alignment tool in an area of interest; pointing a laser that emits a laser beam at the ball of the alignment tool; creating a diffraction pattern on the crosshair by diffusing the laser beam at the ball; and adjusting the laser until the diffraction pattern is visible in the center of the crosshair of the alignment tool. The alignment tool includes a ball and a crosshair having a center.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides an alignment quality indicator that may be used in conjunction with radiographic inspection techniques. One embodiment of the present invention enables 3-dimensional alignment of a radiation source, such as a x-ray tube or a gamma ray source, with small width defects while eliminating the need to take multiple exposures as typically done in the prior art. Furthermore, one embodiment of the present invention provides alignment quality feedback to the interpreter of the radiographs, such as an inspector or engineer. In one embodiment, the present invention provides an alignment tool that may be visible in a radiograph after being exposed to radiation and that may provide proof of alignment quality by showing a ball positioned in the center of a crosshair, while prior art alignment aides do not have these radiographic qualities. An embodiment of the present invention provides an alignment tool that is suitable for, but not limited to, applications in the aerospace industry, such as nondestructive testing and evaluation of airframes during aircraft manufacturing, maintenance, and repair. The alignment tool, as in one embodiment of the present invention, may be used, for example, for crack and or gap detection during fastener inspection and during the inspection of aileron hinges of aircraft airframes using radiographic techniques.

In one embodiment, the present invention provides an alignment tool that includes a ball positioned in a certain distance over a crosshair. The alignment tool as in one embodiment of the present invention may be placed on a surface of a part to be inspected in an area of interest. A focal spot centering laser, which is aligned with the focal spot of an x-ray tube or other radiation source, may be pointed at the ball creating a diffraction pattern on the crosshair. The laser may be adjusted such that the diffraction pattern of the ball is positioned in the center of the crosshair. By aligning the laser with the focal spot of the radiation source, such as an x-ray tube, as in one embodiment of the present invention, the radiation source may be aligned to be pointing in the direction where a defect, such as a crack, gap, or other condition is expected. Using a ball and a crosshair, as in one embodiment of the present invention, may enable three-dimensional aligning of the radiation source, which is not possible using a prior art alignment aide—such as one that includes a plurality of metal pins arranged in adjacent right triangle relation.

In one embodiment, the present invention provides an alignment quality indicator that provides feedback to the interpreter of radiographs taken during the inspection, such as an inspector or an engineer. By taking an exposure of the alignment quality indicator after aligning the radiation source, the obtained radiograph may be used as proof of the alignment quality, while prior art radiographic alignment aides do not provide feedback of the alignment quality that is visible in a radiograph due to their poor radiographic qualities. Consequently, one embodiment may improve inspection confidence over that of prior art radiographic inspection techniques. By taking a radiographic exposure of the area to be inspected with the alignment tool positioned on the part to be inspected in the area of interest after aligning the radiation source, such as an x-ray tube, a permanent record of the exposure may be created that indicates the quality of the alignment. If properly aligned, the ball will appear in the center of the crosshair on the radiographic film. After removing the alignment tool, an exposure may be taken from the area of interest with the intended condition. Consequently, the currently existing need to take multiple exposure of an intended condition can be eliminated while the alignment quality may be not only improved but also recorded providing much needed feedback to an inspector of the radiographs.

In one embodiment, the present invention provides a radiographic inspection process that enables accurate three-dimensional alignment of a radiation source, such as an x-ray tube with an area of interest of a part to be inspected as well as alignment quality feedback to an inspector of the radiographs taken during the inspection process. By using the alignment tool as in one embodiment of the present invention in combination with a focal spot centering laser positioned at the exit point of the x-ray tube a highly accurate alignment of the x-ray tube may be achieved and taking multiple exposures of the area of interest as done in prior art may be avoided. By eliminating the currently existing need for repetitive exposures to achieve proper alignment the inspection cycle time and the inspection costs may be reduced.

Figure 1A:
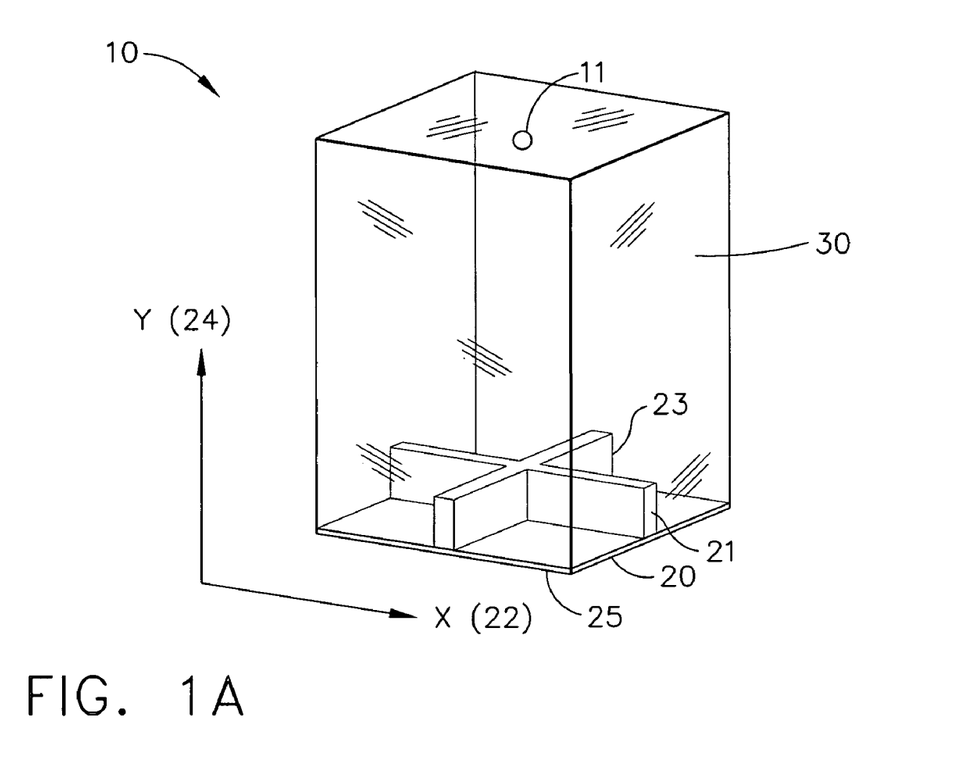
FIG. 1a is a perspective view of an alignment tool according to one embodiment of the present invention.
Figure 1B:
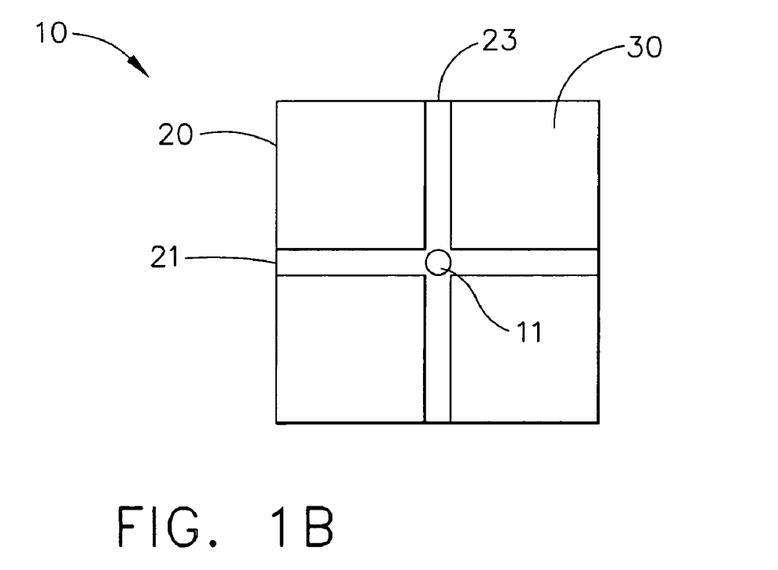
FIG. 1b is a top view of the alignment tool according to one embodiment of the present invention.
Figure 1C:
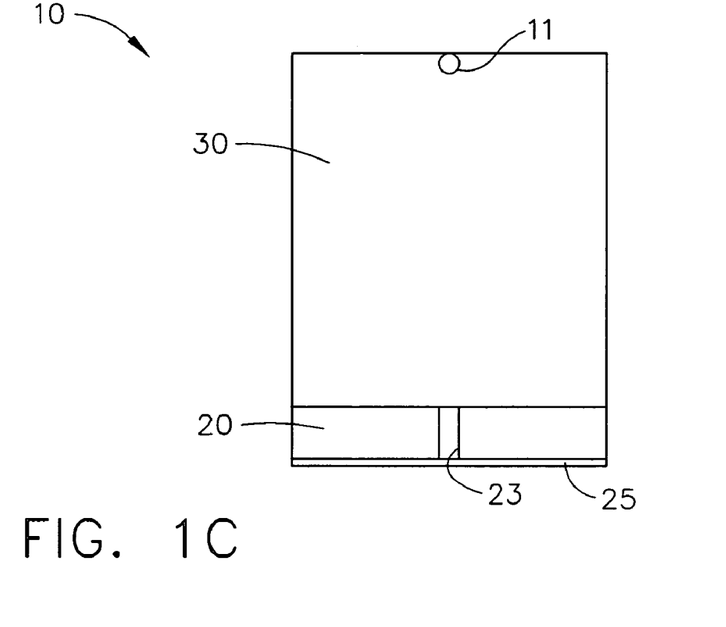
FIG. 1c is a front view of the alignment tool according to one embodiment of the present invention.
Figure 2:
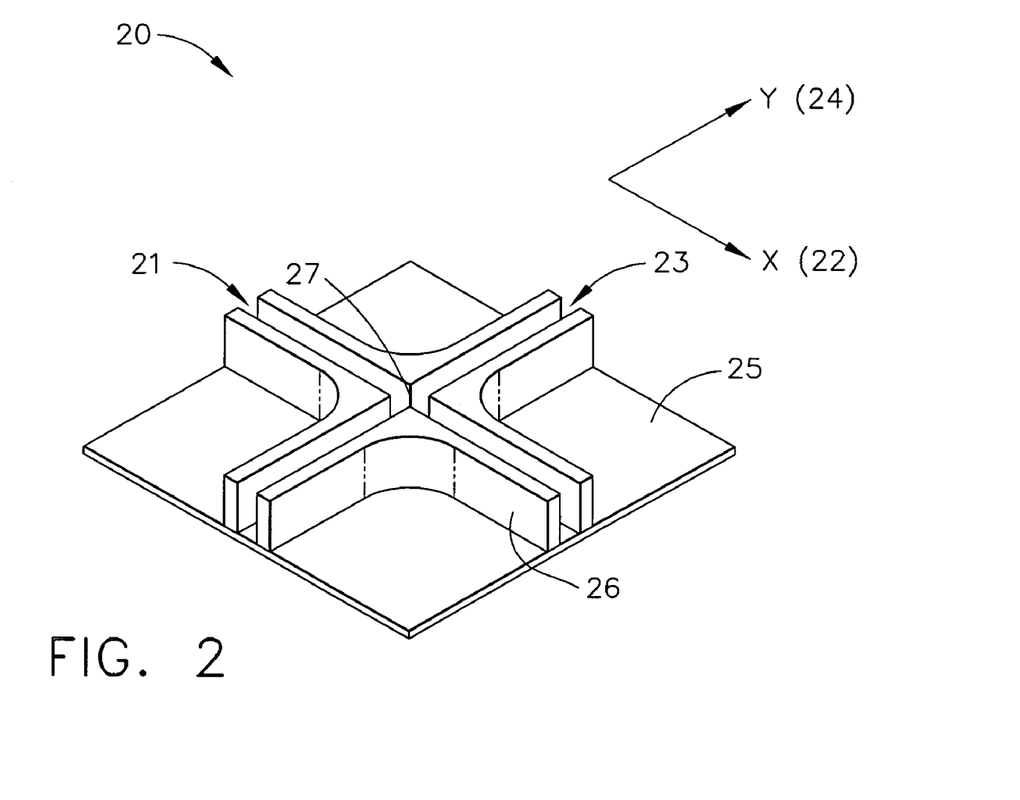
FIG. 2 is a perspective view of a base of the alignment tool according to one embodiment of the present invention.
Figure 3:
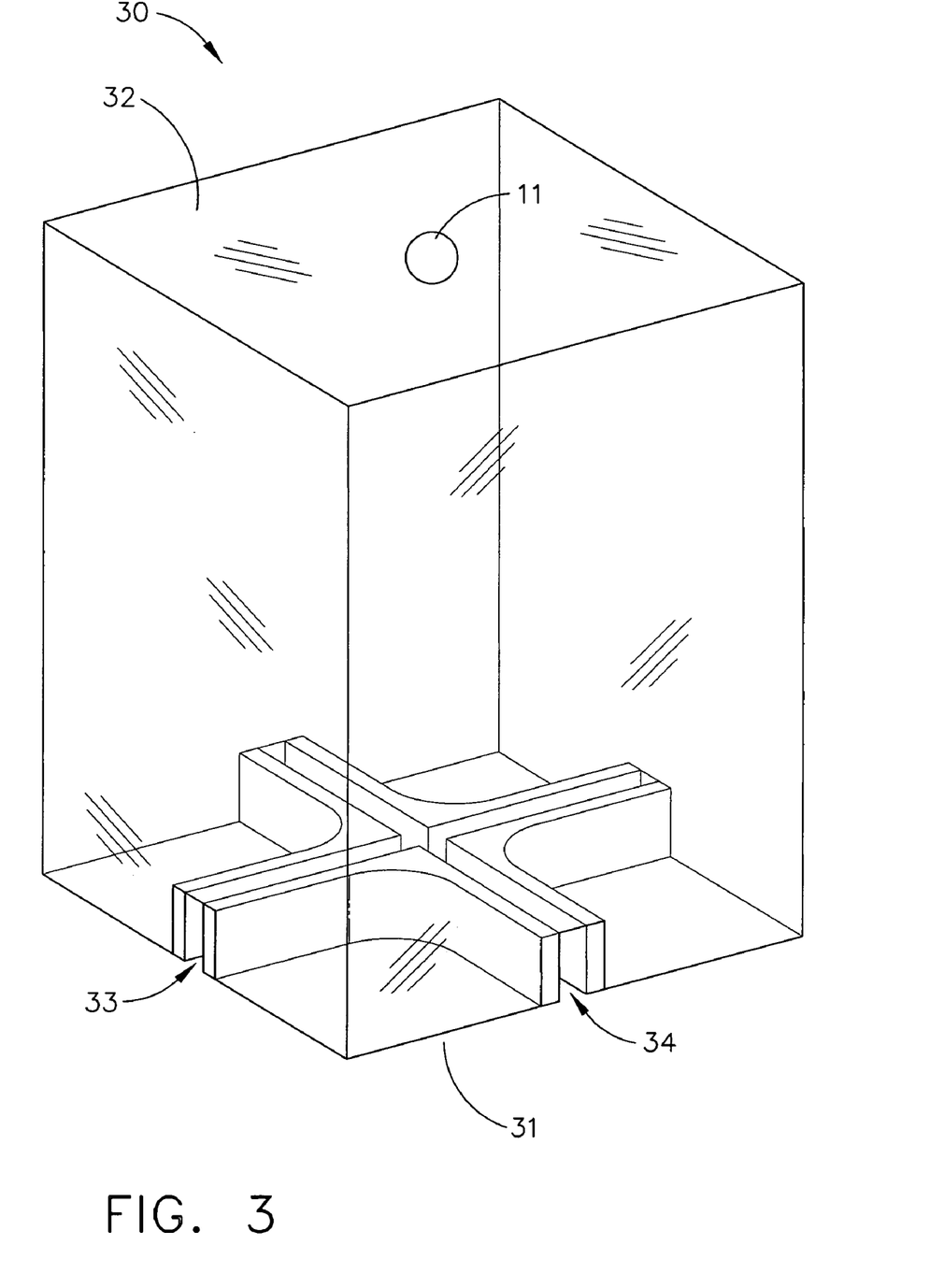
FIG. 3 is a perspective view of a column of the alignment tool according to one embodiment of the present invention.
Figure 4:
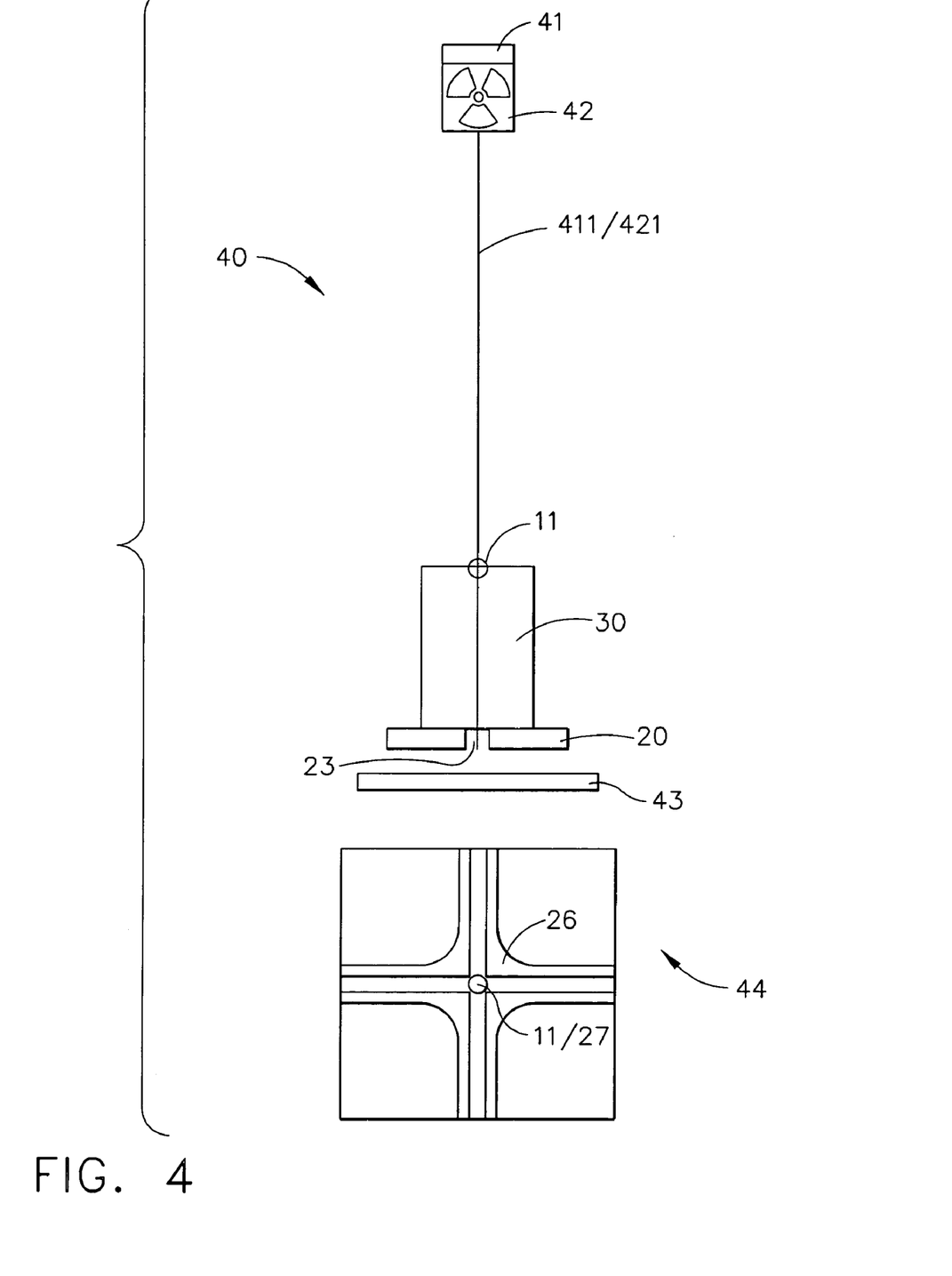
FIG. 4 is a side view of a first implementation of an alignment tool according to another embodiment of the present invention.
Figure 5:
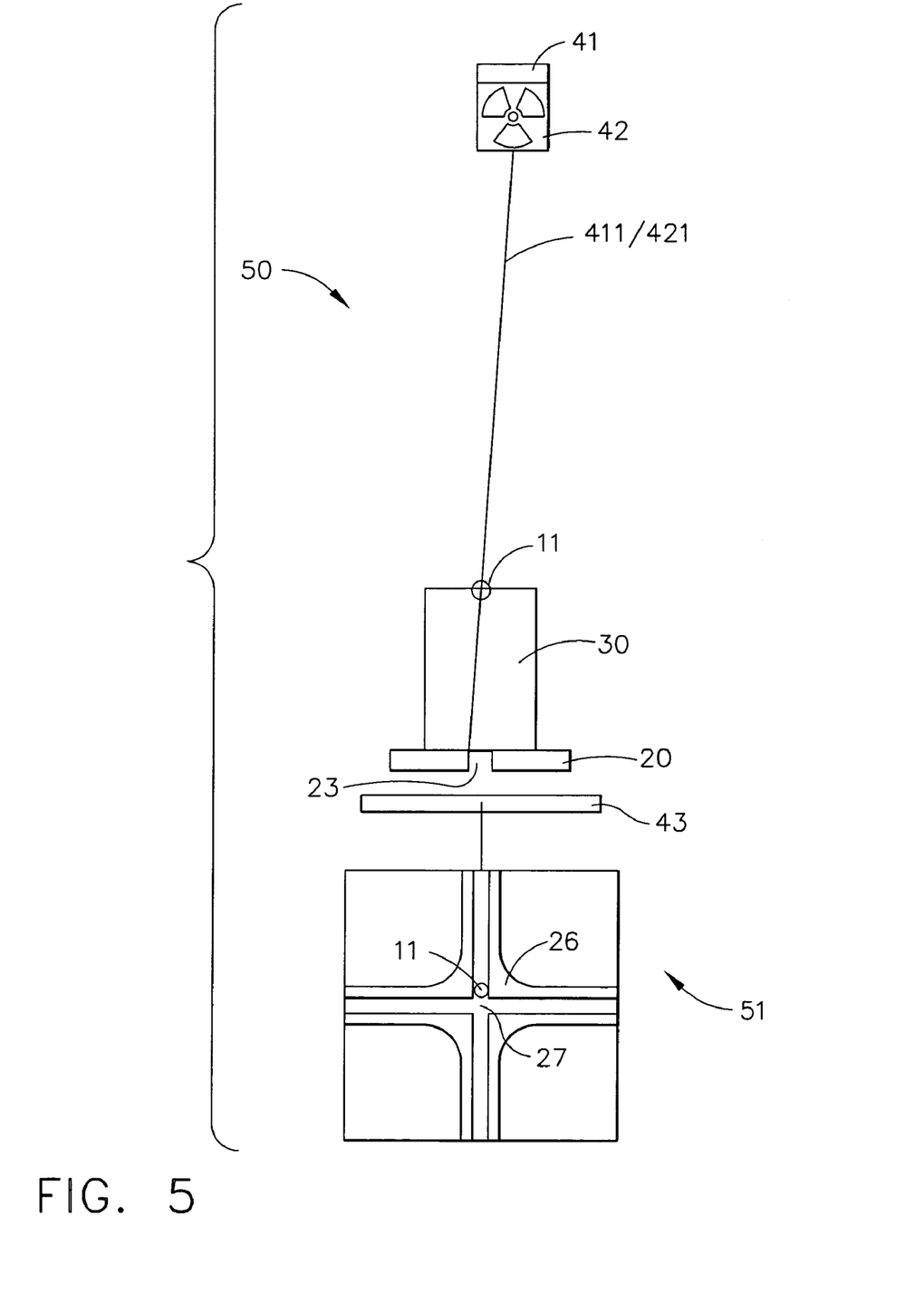
FIG. 5 is a side view of a second implementation of an alignment tool according to one embodiment of the present invention.

Referring now to FIGS. 1a, 1b, and 1c, an alignment tool 10 is illustrated according to one embodiment of the present invention. The alignment tool 10 includes a base 20, a column 30, and a ball 11. The base 20, also shown in detail in FIG. 2, may be manufactured, for example, from aluminum due to the high material density of the aluminum. The base 20 may be manufactured from a material having a high material density in order to make the ball 11 visible in a radiograph obtained after radiographic exposure of the alignment tool 10. Manufacturing the base 20 from other materials than aluminum that have a high material density may be possible. A channel 21 that extends in x-direction (22) and a channel 23 that extends in y-direction (24) may be manufactured on to a base plate 25. Channel 21 and channel 23 may form a crosshair 26 having a center 27 where channel 21 crosses channel 23. The center 27 may be located at equal distances on all sides of the crosshair 26. The base plate may have preferably a square shape (as shown in FIGS. 1a, 1b, and 2) but is not limited to a square shape. The base 20 may be a male portion of the alignment tool 10. The column 30, also shown in detail in FIG. 3, may be machined from an optically transparent material, for example, from an optically transparent polymer material, such as Plexiglas® or Lexan®. The column 30 may be machined from an optically transparent material such that a pattern created by a laser 41 on the base 20 may be visible through the column 30 (as shown in FIGS. 4 and 5). The column 39 may be designed as a female portion of the alignment tool 10. The column 30 may have, for example, a rectangular shape (as shown in FIGS. 1a and 3) or a cylindrical shape. The shape of the base 20 and the column 30 and, therefore, of the alignment tool itself, is not critical to the present invention as in one embodiment. The column 30 may extend longitudinally from a first end 31 to a second end 32. The column 30 may be manufactured to include cutouts 33 and 34 at the first end 32 that may receive the channels 21 and 23 of the base 20. The first end 31 of column 30 may be attached to the base 20 and may be in a fixed connection with the base 20. The crosshair 26 may be visible from the second end 32 of the column 30. The length of the column 30, which may be the distance from the first end 31 to the second end 32, may be chosen according to the inspection task. The ball 11 may be positioned within the column 30 at the second end 32 opposite to the base 20, as shown in FIGS. 1a and 3. The ball 11 may further be positioned directly above the center 27 of the crosshair 26, as shown in FIG. 1b. The distance of the ball 11 to the crosshair 26 may be equal to the length of the column 30, which may be the distance from the first end 31 to the second end 32, may be chosen according to the inspection task. The size of the ball 11 may be preferably chosen to fit exactly into the center 17 of the crosshair 26, as shown in FIG. 1b. Furthermore, the size of the ball 11 may be smaller than the spot size of the laser 41 (shown in FIGS. 4, 5, 6, and 7).

Referring now to FIG. 4, a first implementation 40 of the alignment tool 10 is illustrated according to another embodiment of the present invention. A focal spot centering laser 41 may be connected to a radiation source, for example, to an x-ray tube 42 such that the laser 41 sits at the exit point of the x-ray tube 42. The laser 41 may be aligned with the focal spot of the x-ray tube 42 and may have a spot size greater than the size of the ball 11. The laser 41 may be positioned at a certain distance (for example, Y' (65) shown in FIG. 6) from the alignment tool 10. The distance Y' (65) (shown in FIG. 6) may depend on the inspection task. The laser beam 411 may be pointed at the ball 11 of the alignment tool 10. At the ball 11 the laser beam 411 may reflect and diffuse. The diffused laser will transmit through the polymer material of the column 30 of the alignment tool 10 and may create a diffraction pattern on the surface of the base 20. The location of the diffraction pattern on the base 20 may be used to determine how to orient the x-ray tube 42. Adjustments to the x-ray tube 42 may be made until the diffraction pattern on the base 20 is located at equal distances on all sides of the crosshair 26 and, therefore, in the center 27 of the crosshair. Once the x-ray tube 42 is aligned, a radiographic exposure may be taken by exposing the alignment tool 10 to x-rays 421. An image of the alignment tool 10 may be recorded with a digital detector 43 (FIG. 4) or on radiographic film (not shown). The digital image 44 of the alignment tool 10, as illustrated in FIG. 4, shows the ball 11 in the center 27 of the crosshair 26. This indicates, that the x-ray tube 42 is properly aligned. The digital image 44 of the alignment tool may serve as a quality indicator of the alignment process and may be used by an interpreter of the radiographs to determine the alignment quality.

Referring now to FIG. 5, a second implementation 50 of the alignment tool 10 is illustrated according to one embodiment of the present invention. As shown in the digital image 51, the x-ray tube 42 has not been aligned properly. The image of the ball 11 does not appear in the center 27 of the crosshair 26. If this improper alignment would be used to take a radiographic exposure of a defect, such as a crack, gap or other condition, the radiographic image would not reflect the correct size of the defect. Consequently, the alignment tool 10 may not only be used to properly align an x-ray tube 42 or any other radiation source with an area of interest of a part to be inspected but may also be used as an alignment quality indicator providing information of proper alignment to an interpreter of the radiograph (such as the digital image 44 shown in FIG. 4 or the digital image 51 shown in FIG. 5) taken.

Figure 6:
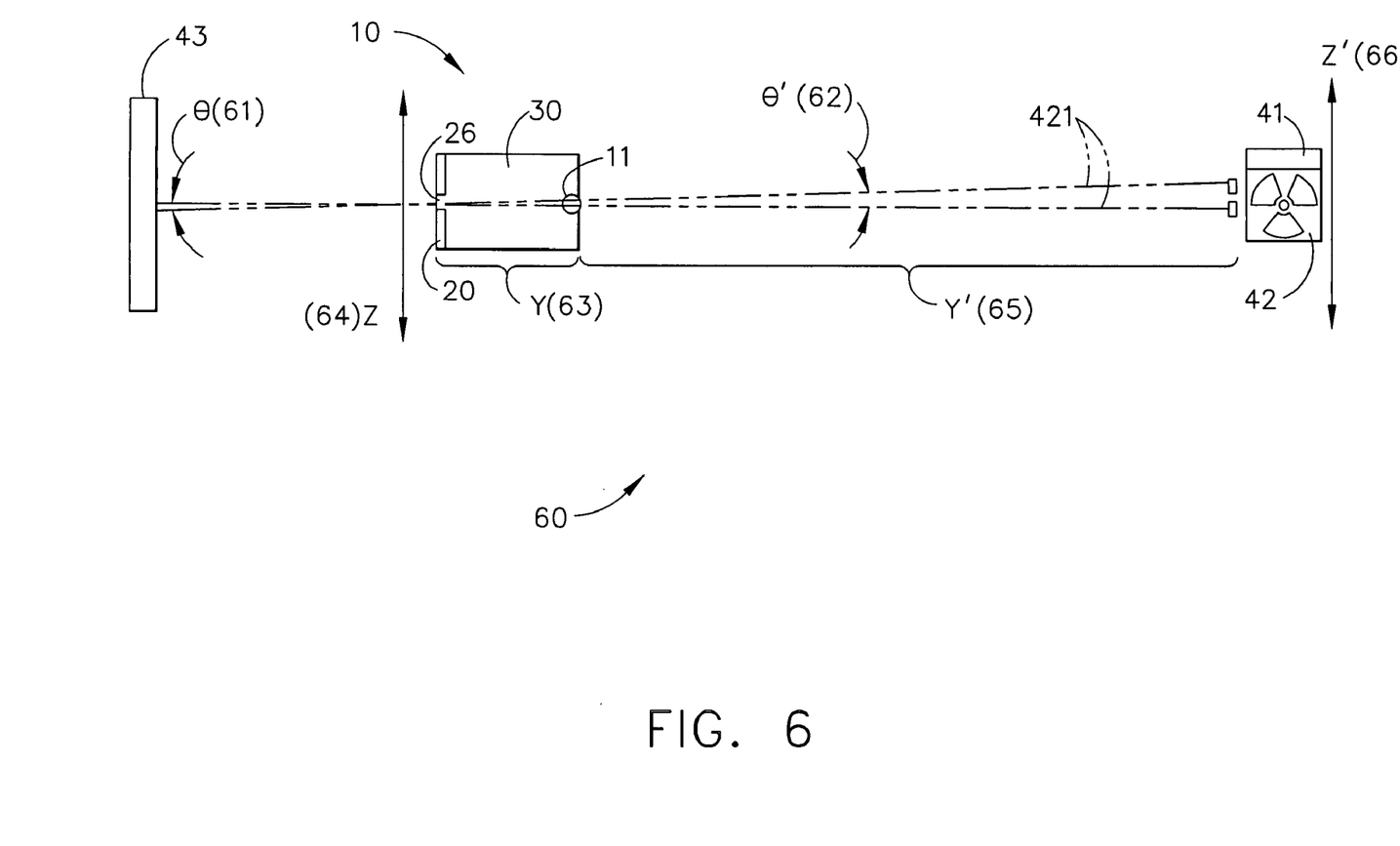
FIG. 6 is a side view of a first operation mode according to another embodiment of the present invention.

Referring now to FIG. 6, a first operation mode 60 is illustrated according to another embodiment of the present invention. The illustration of the first operation mode 60 shows the x-ray tube 42 properly aligned with the alignment tool 10. The digital image that may be recorded with the digital detector 43 may be the same as the digital image 44 shown in FIG. 4, where the image of the ball 11 is located in the center 27 of the cross hair 26. When the x-ray tube 42 is properly aligned, the angles $\theta$ (61) and $\theta'$ (62) may be identical and may be used to calculate a two-dimensional resolution. Since $\tan \theta = Z/Y$ and $\tan \theta' = Z'/Y'$, the distances Z (64), Y (63), Z' (66), and Y' (65) have the following correlation: Z/Y=Z'/Y'; wherein Y (63) may be the length of the alignment indicator 10, Z (64) may be the measurable resolution on the digital detector 43 or a film, Y' (65) may be the distance from the exit point of the x-ray tube 42 to the ball 11 and, therefore, to the second end 32 of the column 30 of the alignment indicator 10, and Z' (66) may be the length of the focal point of the x-ray tube 42. The length Y (63) of the alignment indicator 10 may be preferably about 2 inches, but may be tailored according to the inspection task. When the parameters Y (63), Z (64), and Y' (65) are known, the distance Z' (66) may be determined. When the parameters Y (63), Y' (65), and Z' (66) are known, the distance Z (64) may be determined. By increasing the length Y (63) of the alignment indicator 10 a higher resolution Z (64) or accuracy of the measurement may be reached. As shown in FIG. 6, the alignment tool 10 may be used as an alignment quality indicator.

Figure 7:
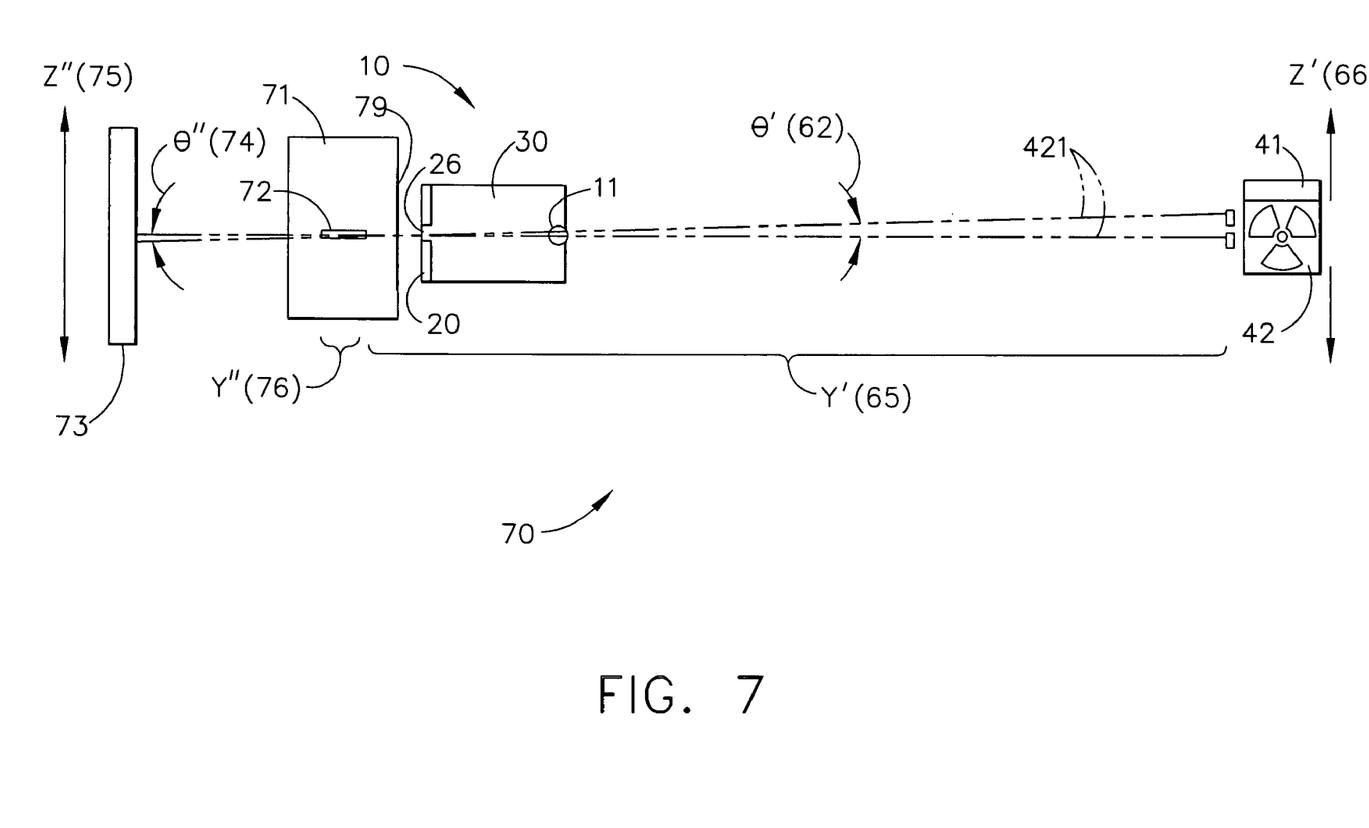
FIG. 7 is a side view of a second operation mode according to one embodiment of the present invention.

Referring now to FIG. 7, a second operation mode 70 is illustrated according to one embodiment of the present invention. FIG. 7 shows the alignment tool 10 placed on the surface of a part 71 to be inspected in an area of interest 79 where the defect 72, for example, a crack, gap or other condition, is suspected. The alignment tool 10 may or may not have contact with the surface of the part 71 to be inspected. To position the alignment tool 10 in the area of interest attachment aids (not shown) may be used. As shown in FIG. 7, the alignment tool 10 may be used to properly align the x-ray tube 42, or any other radiation source, in an area of interest 79 of the part 71 to be inspected. After the alignment, when a laser diffraction pattern of the ball is positioned in the center 27 of the cross hair 26, the laser may be turned off and the alignment indicator 10 may be removed from the part 71 or at least moved out of the area of interest 79 that is going to be inspected. If desired, a radiographic exposure may be taken after the alignment of the x-ray tube 42 while the alignment indicator 10 is still positioned on the surface of the part 71. Such radiograph may be used to indicate the alignment quality. After the removal of the alignment tool 10 from the part 71, a radiographic exposure may be taken of the part 71. If the x-ray tube 42 was properly aligned with the area of interest 79, an image of the defect 72 will occur in a digital image recorded with a digital detector 73 or on a radiographic film that allows determination of the real size of the defect 72.

When the x-ray tube 42 is properly aligned over the defect 72, the angles θ" (74) and θ' (62) may be identical and may be used to calculate the dimensions of the defect 72, as shown in FIG. 7. Since tan θ"=Z"/Y" and tan θ'=Z'/Y', the distances Z" (75), Y" (76), Z' (66), and Y' (65) have the following correlation: Z"/"Y=Z'Y'; wherein Z" (75) may be the length of the defect 72 in vertical direction in the digital image 73 or on a radiographic film, Y" (76) may be the length of the defect 72 in horizontal direction, Y' (65) may be the distance from the x-ray tube 42 to the defect 72, and Z' (66) may be the length of the focal point of the x-ray tube 42. Improper alignment of the x-ray tube 42 may result in an incorrect identification of the defect 72, since the defect 72 may appear smaller in the radiographic image.

Figure 8:
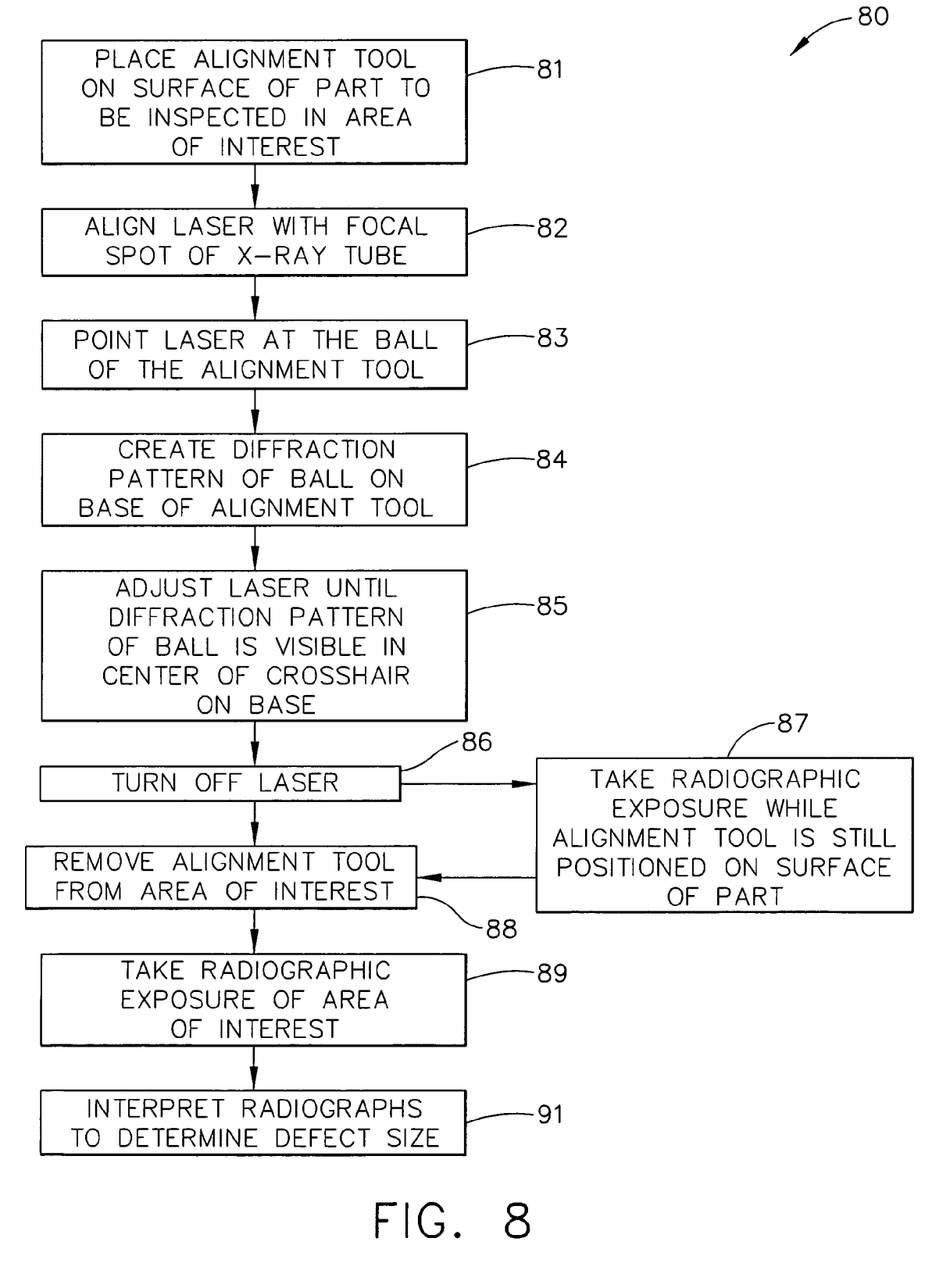
FIG. 8 is a flow chart of a radiographic inspection process according to another embodiment of the present invention.

Referring now to FIG. 8, a radiographic inspection process 80 is illustrated according to another embodiment of the present invention. The process 80 may include the steps of: placing an alignment tool 10 in an area of interest 79 (step 81), for example, on the surface of a part 71 to be inspected, and aligning a laser 41 that with the focal spot of an x-ray tube 42 (step 82) that is positioned in a distance Y' (65) from the part 71 (shown in FIG. 7). In step 83, the laser 41 that emits a laser beam 411 may be pointed at the ball 11 of the alignment tool 10. The laser beam 411 may be reflected and diffused at the ball 11 and a diffraction pattern of the ball 11 may be created on the base 20 of the alignment tool 10 in step 84 (shown in FIGS. 4 and 5). In step 85, the laser 41 may be adjusted until the diffraction pattern of the ball 11 is visible in the center 27 of the crosshair 26 on the base 20 (shown in FIG. 4). After turning off the laser 41 in step 86, a radiographic exposure of the alignment tool 10, which is still positioned on the surface of the part 71, may be taken in step 87. The obtained radiograph, such as the digital image 44 shown in FIG. 4, may be used as a quality indicator and may provide feedback of the alignment to an interpreter of the radiograph. Step 87 may not always be necessary. The alignment tool 10 may be removed from the part 71 or at least moved out of the area of interest 79 in step 88. Now, a radiographic exposure of the area of interest 79 may be taken in step 89. In step 91, the obtained radiograph may be evaluated and interpreted to determine the size of the defect 71 (shown in FIG. 7).

It should be understood, of course, that the foregoing relates to exemplary embodiments of the invention and that modifications may be made without departing from the spirit and scope of the invention as set forth in the following claims.

I claim:

1. An alignment tool, comprising:
   a base including a crosshair having a center;
   a column machined from an optically transparent material, wherein said column has a first end and a second end, wherein said first end of said column is attached to said base, and wherein said crosshair is visible from said second end of said column; and
   a ball, wherein said ball is positioned within said column at said second end, and wherein said ball is positioned above said center of said crosshair; wherein
   said ball is configured to create a diffraction pattern on said crosshair in response to a laser beam entering said second end of said column, said diffraction pattern indicating alignment of said laser beam relative to an area of interest.

2. The alignment tool of claim 1, wherein said base is manufactured from a material having a high material density.

3. The alignment tool of claim 1, wherein said base is manufactured from aluminum.

4. The alignment tool of claim 1, wherein said column is machined from an optically transparent polymer material.

5. The alignment tool of claim 1, wherein said base includes a first channel extending in an x-direction and a second channel extending in a y-direction, wherein said first channel crosses said second channel forming said crosshair, and wherein said center of said crosshair is located at the point where said first channel crosses said second channel at equal distances on all sides of said crosshair.

6. The alignment tool of claim 1, wherein said column extends longitudinally from said first end to said second end for a distance, and wherein said distance is equal to the distance of said ball from said crosshair, and wherein said distance is chosen according to an inspection task.

7. The alignment tool of claim 1, wherein said column includes cutouts located at said first end, wherein said cutouts receive said first channel and said second channel of said base.

8. The alignment tool of claim 1, wherein the distance from said first end to said second end of said column is chosen according to an inspection task.

9. The alignment tool of claim 1, wherein said ball has a size that is smaller than the spot size of a laser.

10. The alignment tool of claim 1, wherein said base is in a fixed connection with said column.

11. An alignment quality indicator, comprising:
a radiation source having a focal point;
a laser aligned with said focal point of said radiation source, said laser being configured to emit a laser beam;
an alignment tool, comprising:
  a base manufactured from a material having a high material density, wherein said base includes a crosshair having a center;
  a column machined from an optically transparent polymer material, wherein said column has a first end and a second end, wherein said first end of said column is attached to said base, and wherein said crosshair is visible from said second end of said column; and
  a ball, wherein said ball is positioned within said column at said second end, wherein said ball is positioned above said center of said crosshair, wherein said laser beam is pointed at said ball, and wherein said ball is configured to create a diffraction pattern on said crosshair in response to the laser beam, said diffraction pattern indicating alignment of said laser beam relative to an area of interest; and
a radiographic detector, wherein said alignment tool is positioned between said radiation source and said radiographic detector.

12. The alignment quality indicator of claim 11, wherein said radiation source is an x-ray tube.

13. The alignment quality indicator of claim 11, wherein said radiation source is a gamma ray source.

14. The alignment quality indicator of claim 11, wherein said laser has a spot size that is larger than the size of said ball of said alignment tool.

15. The alignment quality indicator of claim 11, wherein said radiographic detector is a radiographic film.

16. The alignment quality indicator of claim 11, wherein said radiographic detector is a digital detector.

17. The alignment quality indicator of claim 11, wherein said laser beam is diffused at said ball of said alignment tool creating said diffraction pattern on said base of said alignment tool, and wherein said diffraction pattern includes a pattern of said ball aligned with said center of said crosshair when said laser beam is aligned with said area of interest.

18. The alignment quality indicator of claim 11, wherein said radiographic detector provides a radiograph of said alignment tool after exposure of said alignment tool to radiation from said radiation source.

19. The alignment quality indicator of claim 18, wherein said radiograph shows an image of said ball in said center of said crosshair if said laser beam is aligned with said area of interest.

20. A radiographic inspection process, comprising the steps of:
placing an alignment tool that includes a ball and a crosshair having a center in an area of interest;
pointing a laser that emits a laser beam at said ball of said alignment tool;
creating a diffraction pattern on said crosshair by diffusing said laser beam at said ball; and
adjusting said laser until a pattern of said ball in said diffraction pattern is visible in said center of said crosshair of said alignment tool.

21. The radiographic inspection process of claim 20, further comprising the steps of:
aligning said laser with a focal point of a radiation source;
removing said alignment tool from said area of interest; and
taking a radiographic exposure from said area of interest.

22. The radiographic inspection process of claim 20, further comprising the step of taking a radiographic exposure of said alignment tool before removing said alignment tool from the area of interest.

23. The radiographic inspection process of claim 20, further comprising the steps of:
obtaining a radiograph from said radiographic exposure of said area of interest;
obtaining a radiograph from said radiographic exposure of said alignment tool; interpreting said radiographs; and
determining the size of a defect visible in said radiograph of said area of interest.

* * * * *